United States Patent [19]

Gil et al.

[11] Patent Number: 5,709,888
[45] Date of Patent: Jan. 20, 1998

[54] HIGH FAT NUTRITIONAL FORMULA FOR INFANTS AND ADULTS

[75] Inventors: Angel H. Gil; Jesus L. Jimenez; Jose C. Moreno, all of Granada, Spain

[73] Assignee: Abbott Laboratories, Abbott Park, Ill.

[21] Appl. No.: 621,368

[22] Filed: Mar. 25, 1996

Related U.S. Application Data

[63] Continuation of Ser. No. 624,230, Dec. 7, 1990, abandoned.

[30] Foreign Application Priority Data

Oct. 30, 1990 [ES] Spain ................ P.90102.759

[51] Int. Cl.$^6$ ............ A61K 35/12; A61K 35/60; A61K 31/70; A61K 31/685; A61K 31/20; A61K 31/07
[52] U.S. Cl. .............. 424/522; 424/523; 514/45; 514/78; 514/560; 514/775
[58] Field of Search .................. 514/775, 560, 514/78, 45; 424/522, 523

[56] References Cited

U.S. PATENT DOCUMENTS

| | | | |
|---|---|---|---|
| 3,873,720 | 3/1975 | Seiguki et al. | 424/312 |
| 4,388,324 | 6/1983 | Horrobin | 424/312 |
| 4,415,554 | 11/1983 | Horrobin | 424/145 |
| 4,526,902 | 7/1985 | Rubin | 514/560 |
| 4,670,285 | 6/1987 | Clandinin et al. | 426/602 |
| 4,758,592 | 7/1988 | Horroben et al. | 514/549 |
| 4,820,731 | 4/1989 | Mascioli et al. | 514/549 |
| 4,826,877 | 5/1989 | Stewart et al. | 514/560 |
| 4,931,468 | 6/1990 | Horrobin | 514/560 |
| 4,948,811 | 8/1990 | Spinner et al. | 514/560 |
| 5,032,585 | 7/1991 | Lichtenberger | 514/78 |
| 5,043,328 | 8/1991 | Weithmann | 514/78 |

FOREIGN PATENT DOCUMENTS

| | | |
|---|---|---|
| 84100207 | 1/1984 | European Pat. Off. . |
| 84303678 | 6/1984 | European Pat. Off. . |
| 85112675 | 10/1985 | European Pat. Off. . |
| 87101310 | 1/1987 | European Pat. Off. . |
| 87308497 | 9/1987 | European Pat. Off. . |
| 89200062 | 1/1989 | European Pat. Off. . |
| 89303040 | 3/1989 | European Pat. Off. . |
| 89313433 | 12/1989 | European Pat. Off. . |
| 433282 | 12/1965 | France . |
| 82 19043 | 11/1982 | France . |
| 86 13928 | 10/1986 | France . |
| 60-49747 | 3/1985 | Japan . |
| 62-258391 | 11/1987 | Japan . |
| PCT/DK86/00116 | 10/1986 | WIPO . |
| PCT/NL88/00058 | 12/1988 | WIPO . |
| PCT/US89/01364 | 3/1989 | WIPO . |

OTHER PUBLICATIONS

Ralph T. Holman, "How Essential Are Essential Fatty Acids?", J. Am. Oil Chemists' Soc., Oct. 1978 (vol. 55), pp. 774A–781A.

Holman et al., "A case of human linolenic acid deficiency involving neurological abnormalities", The American Journal of Clinical Nutrition 35, Mar. 1982, pp. 617–623.

Bjerve et al., "Alpha–linolenic acid deficiency in patients on long–term gastric–tube feeding: estimation of linolenic . . . man$^{1-3}$", Am. Journal of Clin. Nutrition, 1987, pp. 66–77.

Bjerve et al., "Alpha–linolenic acid deficiency in man: effect of ethyl linolenate on plasma . . . prostanoids$^{1-3}$", American Journal of Clinical Nutrition, 1987, pp. 570–576.

Bjerve et al., "α–Linolenic acid and long–chain ω-3 fatty acid supplementation in three patients with ω-3 fatty supplementation in three patients . . . formation$^{1-3}$", American Journal Clin. Nutr., 1989, pp. 290–300.

Bjerve, "ω3 Fatty Acid Deficiency in Man; . . . ω3 Fatty Acids", World Rev. Nutr. Diet, Basel, Karger, 1991, vol. 66, pp. 133–142.

Koletzko et al., "Effects of dietary long–chain polyunsaturated fatty acids on the essential fatty acid status of premature infants", European Journal of Pediatrics, (1989) 148, pp. 669–675.

Koletzko et al., "Effects of Dietary Long–Chain Polyunsaturated Fatty Acids on the Essential Fatty . . . Infants," European Journal of Pediatrics (1989) 148: pp. 669–675.

Neuringer et al., "Biochemical and functional effects of prenatal and postnatal . . . in rhesus monkeys", Proc. Natl. Acad. Sci, vol. 83, pp. 4021–4025 (1986).

Neuringer et al., "n–3 Fatty Acids in the Brain and Retina; Evidence for Their Essentiality", Nutrition Reviews, vol. 44, No. 9, Sep. 1986, pp. 285–294.

Bourre et al., "Essentiality of ω3 Fatty Acids for Brain Structure and Function", World Rev. Nutr. Diet., 1991; 66: pp. 103–117.

Galli et al., "Dietary ω3 and ω6 Fatty Acids", Plenum Press, 1988, pp. 159–175.

I. Masi, et al., "Diets Rich in Saturated, Monounsaturated and Polyunsaturated Fatty Acids . . . in Rabbits", Ann. Nutr. Metab., 1986, 30: 66–72.

(List continued on next page.)

Primary Examiner—Theodore J. Criares
Attorney, Agent, or Firm—Donald O. Nickey; Thomas D. Brainard; Watson T. Scott

[57] ABSTRACT

The present invention provides a new fat mixture for infant and adult nutrition which possesses adequate levels and ratios of polyunsaturated fats and long chain polyunsaturated fats. These fat mixtures possess adequate levels of phospholipids and an adequate relationship between oleic acid, linoleic acid and α-linolenic acid as well as adequate levels of long chain polyunsaturated fatty acids of both the n6 and n3 series. In addition, the fat mixtures of the present invention possess an adequate ratio of arachidonic acid (20:4n6) to docosahexaenoic acid (22:6n3). These fat mixtures are modeled on the fat content of human milk for infant diets and on the mediterranean diet for adult nutritional products. Diets containing these mixtures promote the growth and development of the infant and contribute to the prevention and treatment of some diseases in adults.

21 Claims, No Drawings

OTHER PUBLICATIONS

Scott M. Grundy, M.D. "Comparacion de Acidos Grasos Monoinsaturados Y Carbohidratos en la Reduccion del Colesterol Plamatico" N. England J. Med 1986 314:745–748.

Ronald P. Mensink "Efecto de los Acidos Grasos Monoinsaturados Versus Carbohidratos Complejos . . . Mujeres Sanons" The Lancet 1987 1:1–7.

Vera M. Marsic, et al. "Monounsaturates and Coronary Heart Disease" SVO Enterprises, Jul. 1990, pp. 1–9.

"Cardiovascular Research Report" American Heart Association, No. 20/Summer 1985, pp. 1–3.

M. Martinez, et al. "Lipids of the Developing Human Retina: I. Total . . . Phosphoglycerides": Journal of Neuroscience Research 20:484–490 (1988).

Ralph T. Holman "Polyunsaturated Fatty Acid Profiles in Human Disease" 1981: 25–42.

E. Cabre, et al. "Polyunsaturated Fatty Acid Deficiency in Liver . . . Malnutrition"; The American Journal of Gastroenterology; vol. 83 No. 7, 1988.

Norman Salem Jr., et al "Growth and Development in Infants" World Rev Nutr Diet 1991; 66: 20–25.

C–C Frank Liu, "Increase in Plasma Phospholipid . . . Administration" Pediatric Research 1987; 22: 292–296.

S.E. Carlson, et al. "Essentiality of w3 Fatty Acids in . . . Infants" Rev Nutr Diet 1991; 66:74–86.

Clandinin, M.T., et al., "Requirements of Newborn Infants for Long Chain Polyunsaturated Fatty Acids", Acta Paqediatr Scand Suppl, vol. 351, pp. 63–71, 1989.

Aggett, P.J., et al., "Comment on the Content and Composition of Lipids in Infant Formulas", Acta Paediatr Scand vol. 80, pp. 887–896, 1991.

Kinsella, John E., et al., "Dietary Polyunsaturated Fatty Acids and Eicosanoids: Potential Effects on the Modulation of Inflammatory and Immune Cells: An Overview", Nutrition, vol. 6, No. 1, pp. 24–44, Jan.–Feb., 1990.

Connor et al., "Essentiality of w3 Fatty Acids: Evidence from the Primate Model and Implications for . . . ", World Rev. Nutr. Diet. Basel, Karger, 1991, vol. 66, pp. 118–132.

"Dietary Long Chain Polyunsaturates for Premature Infants", Journal of Pediatric Gastroenterology and Nutrition (1987) 6: pp. 997–999.

Article published in *European Journal of Clinical Nutrition* entitled, "Changes in the Fatty Acid Profiles of Plasma Lipid Fractions Induced by Dietary Nucleotides in Infants Born at Term", (1988), vol. 42 pp. 473–481.

HIGH FAT NUTRITIONAL FORMULA FOR INFANTS AND ADULTS

This is a continuation of application Ser. No. 07/624,230, filed Dec. 7, 1990, abandoned.

The present invention is related to the composition of specific high fat formulas which can be used in an isolated form or as part of dietary products. Examples of such dietary products are infant formulas and dietetic products which can be used to feed both healthy and ill individuals.

BACKGROUND OF THE INVENTION

At present a variety of families of polyunsaturated fatty acids (hereinafter PUFA's) are known to exist. The n6 series, which is considered essential to human life, consists of fatty acids which are derived from linoleic acid.

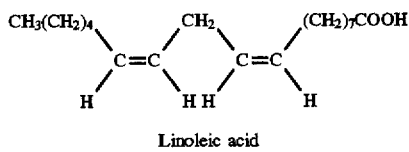

Linoleic acid

The n3 series of polyunsaturated fatty acids, which is now considered essential during early postnatal life in human beings, is derived from α-linolenic acid.

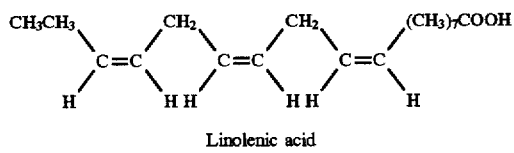

Linolenic acid

The n9 family of fatty acids is derived from oleic acid and the n7 series is derived from palmitoleic acid. These two families can be synthesized endogenously.

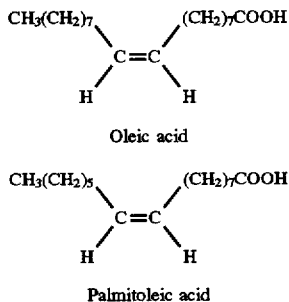

Oleic acid

Palmitoleic acid

Long chain PUFAs are those which contain more than 18 carbon atoms and are synthesized from the precursor polyunsaturated fatty acids via a successive desaturation and elongation process. Each of these families includes fatty acids with similar chain lengths and unsaturation levels. However, none of the members of one family are exactly the same as the corresponding members of the other family.

The families of polyunsaturated fatty acids are unique. They are metabolically derived from different precursors and can not be interconverted. In addition, each type of fatty acid has a different function in the human body and they are not interchangeable.

There is a standard nomenclature for referring to polyunsaturated fatty acids by the chain length, the number of unsaturations and the family to which the fatty acid belongs. For example, the notation (18:2n6) represents linoleic acid. The first number is the length of the carbon backbone. The second number is the number of double bonds present in the fatty acid and the final letter/number designation discloses the family to which a particular fatty acid belongs. Other representations of common fatty acids using this nomenclature are α-linolenic acid (18:3n3) and oleic acid (18:1n9).

A competition is known to exist between linoleic acid (18:2n6), linolenic acid (18:3n3) and oleic acid (18:1n9) for the enzyme Δ 6-desaturase. This enzyme exhibits a strong affinity for α-linolenic acid. Studies have demonstrated that the ratio of linoleic acid (18:2n6) to α-linolenic acid (18:3n3) influences the composition of membranes. Specifically the ratio influences the metabolites of the n6 and n3 series which are involved in membrane composition.

A high ratio of linoleic acid (18:2n6) to α-linolenic acid (18:3n3) in the diet can suppress the elongation and desaturation of α-linolenic acid (18:3n3) to its long chain metabolites. In addition, a high value for this ratio has been shown to increase the unfavorable accumulation of n6 series long chain metabolites in body tissues. It has also been demonstrated that desaturation and elongation of linolenic acid is prevented by the presence of an excess of linoleic acid (18:2n6) and that 6-unsaturation is inhibited by the presence of superior homologues of the n6 and n3 series. In addition, the long chain polyunsaturated fatty acids eicosapentaenoic acid (20:5n3) and docosahexaenoic acid (22:6n3) are competitive inhibitors with cyclo-oxygenase and lipooxygenase for arachidonic acid (20:4n6). This affects the production of prostaglandins, thromboxanes and leucotrienes of the series 2.

The principal lipids found in animal membranes are cholesterol and phospholipids. The ratio of these components is a determining factor in the degree of membrane fluidity and functionality. The contribution of phospholipids to the membrane fluidity will depend on the equilibrium between different phospholipids and the nature of the fatty acids.

Specifically, the dietary equilibrium between fatty acids of the n6 and n3 series is a significant factor in the regulation of the composition of fatty acids in membranes. In addition the amount of oleic acid intake affects the conversion of linoleic acid (18:2n6) and α-linolenic acid (18:3n3) into their corresponding long chain PUFAs. This ratio also affects the composition of membrane phospholipids. The ratio of oleic acid (18:1n9) to α-linolenic acid (18:3n3) is an important factor for determining the composition of fatty acids in a membrane.

The accumulation of docosahexaenoic acid (22:6n3) fatty acids in membranes, particularly those of the gray matter of the cerebrum and in the retina, can be detrimentally lowered by an increase in the ratio of linoleic acid (18:2n6) to α-linolenic acid (18:3n3) in the diet. For example, safflower oil, sunflower oil and other fats which possess a high ratio of linoleic acid (18:2n6) to α-linolenic acid (18:3n3) increase the levels of 22:5n6 fatty acids, created from linoleic acid (18:2n6), in the retina and cerebrum. This ratio also limits the amount of docosahexaenoic acid (22:6n3) which is synthesized from α-linolenic acid.

In addition, a diet based on soy oil or linseed oil, which possesses a low ratio of linoleic acid (18:2n6) fatty acid to α-linolenic acid (18:3n3), increases the content of eicosapentaenoic acid (20:5n3) present in the phospholipids but not the docosahexaenoic acid (22:6n3) content. This suggests the existence of a low level of 4-desaturase activity in humans.

Artificial formulas on the market today, both for adult and infant nutrition, are usually characterized by relatively low levels of oleic acid and high levels of linoleic acid. Most of them do not contain α-linolenic acid and also do not contain long chain polyunsaturated fatty acids of the n3 and n6 series especially a arachidonic acid (20:4n6) and docosahexaenoic acid (22:6n3).

For example, British patent UK 6B 2067587 B, discloses a fat mixture for infant nutrition products which is composed of 10–15% of lauric oil, (coconut, babasu and palm kernel), 20–50% of palm oil, 10–25 % of oleic oils (olive oil, oleo), and 0.20% of linoleic oil (corn, soybean, sunflower or safflower).

There are several problems with the British patent's fat mixture for infant nutrition products. First, it has a low content of α-linolenic acid (18:3n3). In fact, the content of α-linolenic acid is not specified in the patent. As a result, there is an inadequate ratio in that formula between oleic acid, linoleic acid and α-linolenic acid. Second, it possesses a high content of lauric acid (12:0), which increases susceptibility towards atherogenesis with use of this diet. The third problem is the British mixture's high level of palmitic acid, which increases the probability of clump formation. This clump formation limits the absorption of fat. Finally, there are no long chain polyunsaturated fatty acids in the British Patent's fat mixture.

Previously, two sources of long chain polyunsaturated fatty acids have been used:

1. Fish: Generally blue fish is used, because it has a higher content of fat as compared to white fish. The fatty acid composition of fish oil is characterized by low levels of saturated fatty acids and low levels of long chain polyunsaturated fatty acids of the n6 series. Fish oil does contain relatively high levels of n3 long chain polyunsaturated fatty acids, particularly eicosapentaenoic acid (20:5n3) and docosahexaenoic acid (22:6n3).

The exclusive utilization of fish oil as a polyunsaturated fatty acid source presents serious problems resulting from the lack of equilibrium in the ratio of n3 and n6 polyunsaturated fatty acids. The ratio of n3 to n6 long chain polyunsaturated fatty acids is very high in fish oil. This leads to a very low value for the ratio of arachidonic acid (20:4n6) to eicosapentaenoic acid (20:5n3) which is not recommended in a general diet. In addition, most types of fish have a high level of eicosapentaenoic acid (20:5n3) and a low level of docosahexaenoic acid (22:6n3). This alters the ratio of eicosapentaenoic acid (20:5n3) to docosahexaenoic acid (22:6n3). This ratio in human milk is about 1:2–3, in contrast, this ratio in fish oil is 2–3:1.

2. Egg: The chemical composition of eggs is characterized by a high level of fat, about 10%, most of which comes from in the yolk. The high percentage of saturated fatty acids in eggs, specifically 36–40% is remarkable. There is practically no α-linolenic acid and there are only very small amounts of long chain polyunsaturated fatty acids of the n6 and n3 types.

The major problem with using egg as a source of long chain polyunsaturated fatty acids is their high level of cholesterol. Eggs have about 500 mg–1000 mg of cholesterol per 100 g of total fat. These cholesterol levels make the use of egg fats unsuitable for adult nutrition products. In addition, the small amount of long chain polyunsaturated fatty acids present in this source makes it necessary to use a large amount of egg fat in artificial formulas and as a result, the economic cost of the formula becomes very high.

Moreover, the effects on the percentage of the plasmatic content of long chain PUFA, in children who have been fed for 21 days with an infant formula that contained PUFA derived from eggs (Diet I), with an infant formula without PUFA (Diet II), and with maternal milk (Diet III), have been described. The plasma percentages of PUFA, specifically of the arachidonic and docosahexaenoic acids, are reflected in the following data:

|  | Arachidonic (20:4n6) | Docosahexaenoic (22:6n3) |
|---|---|---|
| Diet III | 1.20 | 0.64 |
| Diet I | 0.90 | 0.41 |
| Diet II | 0.49 | 0.26 |

In this diagram it can be seen that, although the diet that was supplemented with PUFA raises the long chain PUFA percentages in plasma, the value is still considerably different from that which exists in milk, at least for these two fatty acids U.S. Pat. No. 4,670,285, describes a fat mixture for infant nutrition based on 75–95% egg yolk lipids. The fat mixture also contains a small amount of coconut and soy oil, and contemplates the possible addition of fish oil.

The use of this fat mixture creates some problems. The cholesterol content of the formula is very high, making the formula unsuitable for adult nutrition. In addition, there is a low ratio of long chain polyunsaturated fatty acids in the yolk lipids. This implies that it is necessary to supply a high proportion of yolk lipids to the total fat in the nutritional products described by the formulas of the '285 patent. To obtain an infant formula which has a fatty acid content comparable to human milk, it becomes necessary to use a large proportion of egg lipids in the total fat mixture (at least 75% of the total fat).

There is a small amount of α-linolenic acid (18:3n3) in the '285 patent fat mixture, 0.3–0.4%. When the '258 fat mixture uses tilapia oil, it does not supply an adequate amount of docosahexaenoic acid (22:6n3) and there is a high ratio of eicosapentaenoic acid (20:5n3) to arachidonic acid (20:4n6).

German patent DE 3603000 describes a fat mixture containing long chain PUFAs which are obtained by mixing animal and/or vegetable fats. The preferred fat mixture from the German patent consists of liver fat, egg lipids, oleo, corn oil, soybean oil, palm oil, palm kernel oil, or coconut oil and fish oil.

The German patent does not disclose an optimal ratio of oleic acid (18:1n9) to linoleic acid (18:2n6) to α-linolenic acid (18:3n3). In addition, the cholesterol content of this fat mixture is very high. As a result, it is not appropriate for adult nutrition, particularly for cardiovascular patients. In addition, the ratio of arachidonic acid (20:4n6) to docosahexaenoic acid (22:6n3) is 2.5/1, which is very high when compared to the value in human milk which is 1:1.

The German patent does not consider the incorporation of the phospholipids into the mixture.

French patent 2553261, describes an artificial milk containing phospholipids from animal placenta, another source of PUFAs. This fat mixture possesses high levels of estrogens which could alter the metabolism of a human being. Comparing this fatty acid composition to human milk, there is a high level of palmitic acid (16:0) and a low level of oleic acid (18:1n9). As far as the long chain polyunsaturated fatty acids, content the French patent's fat mixture does not contain α-linolenic acid (18:3n3) and the level of arachidonic acid (20:4n6) is very high. This results in the ratio of arachidonic acid (20:4n6) to docosahexaenoic acid (22:6n3), 5:1, being very high compared to the range of values in human milk (0.1–1:0.1–1).

Taking into account the important role of the oleic acid (18:1n9), linoleic acid (18:2n6) and α-linolenic acid as regulators of the formation of long chain polyunsaturated and the metabolism of eicosanoids, it would be desirable to know the correct dietary levels of these compounds in order to maintain the membranes. Since no direct data is available about these levels, the desired information can be obtained through examination of other factors. For example, the composition of human milk provides a guide to the desired fatty acid intake for infant nutrition. The dietary intake of fatty acids in populations with a low risk of cardiovascular disease, such as mediterranean countries, provides a guide for adult nutrition.

Although oleic acid is not essential for humans, it plays an important role in the maintenance of the membrane structure. In addition, oleic acid intake brings about changes in fat absorption and cholesterol metabolism. Infants which are fed a diet of artificial formulas in which linoleic acid is the predominant fatty acid, possess plasma cholesterol levels which are lower than those of infants fed with an artificial formula in which oleic acid is the predominant fatty acid (110 mg/dl versus 133 mg/dl respectively). In addition, infants who are fed artificial formulas where oleic acid was the predominant fatty acid displayed higher HDL-cholesterol levels and had higher levels of apoproteins A-I and A-II than those infants which received formulas wherein linoleic acid was the predominant fatty acid. In addition, the cholesterol ratio of LDL-VLDL to HDL was found to be lower in those children who received the formula in which oleic acid predominates.

Currently, monounsaturated fatty acids (MUFA's-oleic and palmitoleic acids) are receiving a great deal of attention with respect to the prevention of some cardiovascular diseases and atherosclerosis. It has been shown that a diet which is enriched with olive oil and contains low levels of saturated fats results in a low incidence of ischemic diseases. Similarly it has also been shown that young humans fed with a diet rich in MUFAs display lower levels of LDL and HDL cholesterol compared to those fed with a control diet or a diet enriched in polyunsaturated fatty acids.

It has also been demonstrated that a diet enriched with olive oil increases the HDL-cholesterol levels in elderly people, while a diet enriched with polyunsaturated fats lowers these levels. The decrease of HDL-cholesterol levels was observed in elderly people and in people with normal or high levels of triglycerides.

Therefore, a desirable fatty acid mixture would be that which contained a ratio of fatty acids, MUFA and PUFA, such that the reducing effects on the level of plasmatic cholesterol would be parallel with the increase of the levels of HDL.

A linoleic acid deficiency has been detected in mammals and in humans who receive fat-free parenteral nutrition and in children who are fed with skim milk. The human requirements for linoleic acid have been estimated to be 1% of the total caloric intake.

Recent studies suggest that linoleic acid per se may not be sufficient to completely satisfy the requirements for essential fatty acids during the fetal period and the early postnatal period. It is possible that a requirement for α-linolenic acid and/or long chain polyunsaturated fatty acids could be established by the use of a fat free diet. Use of a fat-free diet could result in the alteration of the distribution of fatty acids in tissues and could also affect the development of normal visual and mental functions in humans.

Recently, it has been demonstrated that in experimental animals that the levels of prostaglandin $PGI_2$, which displays anticlotting properties, are increased when the diet is enriched in olive oil, and are decreased when the diet is enriched with corn oil. At the same time, lower levels of thromboxane $TXB_2$ are found in animals which receive a diet enriched in olive oil compared to animals which received a diet enriched with PUFAs.

It is known that the long chain fatty acids eicosatrienoic acid (20:3n6), arachidonic acid (20:4n6) and eicosapentaenoic acid (20:5n3) are the precursors of the three different prostaglandin series and other related eicosanoids. The products display specific properties and play an important role in the regulation of many physiological functions. As a result, alteration of the proportion of these fatty acids in the diet may cause changes in the composition of tissue membranes and in the individual's physiology.

On the other hand, providing an adequate supply of these long chain fatty acids and an adequate supply of docosahexaenoic acid (22:6n3), which is an important compound in the development of the cerebrum and the retina, could be critical in human development. Again, human milk and the so-called "mediterranean diet" provide models of compositions for fatty acids in the diet.

It has recently been demonstrated that pre and postnatal children which were malnourished exhibited a significant decrease in the docosahexaenoic acid (22:6n3) levels in the retina. This was particularly true for children who were fed with a diet in which the ratio of n6 to n3 fatty acids was altered.

Long chain polyunsaturated fatty acid supplementation in the diet is especially important where some particular diseases are present, such as cirrhosis and Crohn's disease. For these diseases, it has been observed that despite a normal linoleic and linolenic acid intake and the existence of the normal levels of these fatty acids in the plasma, there is an alteration observed in the profiles of the long chain polyunsaturated fatty acid of the n3 and n6 series. This suggests that the diseases could cause an alteration in the mechanism of desaturation and/or elongation mechanisms of the precursors. In these situations, it would be especially important to incorporate preformed long chain polyunsaturated fatty acids into the diet.

In recent years a number of studies have considered the potential negative effects that could occur from an excessive amount of PUFAs in the diet. Although the long term effects have not been established, the short term effects seems to indicate that such an excess increases the degree of unsaturation of membrane lipids, with a corresponding increase of the susceptibility of these lipids to oxidation, and an increase in tocopherol requirements. Epidemiological studies have been conducted which suggest that an excess of PUFA's intake could enhance the effects of known carcinogens. A relationship has also been shown between an excessive intake of PUFAs and breast cancer. In addition, an increase in lipid peroxidation has also been observed with the presence of an excess of polyunsaturated fatty acids in the diet. This peroxidation could be responsible for the high incidence of tumors.

The presence of an excess of arachidonic acid, the precursor of the series 2 eicosanoids, or an excess of its precursor, linoleic acid, may lead to an increase in thrombogenesis, a decrease in bleeding time, an increase in the inflammatory response of polymorphonuclear monocytes and leukocytes, as well as an increase in smooth muscle reactivity to allergies. In contrast, a diet predominantly based on long chain PUFAs of the n3 series, such as the diet of the Eskimos, produce an increase in bleeding time, and a low incidence of cardiovascular disease, such as, atherosclerosis, arthritis, asthma and other diseases. This is due to the fact that these long chain PUFAs of the n3 series are the precursors for the series 3 eicosanoids.

SUMMARY OF THE PRESENT INVENTION

The present invention provides a new fat mixture which possesses adequate levels and ratios of polyunsaturated fats and long chain polyunsaturated fats. This fat mixture can be used in nutritional formulas for adults and infants in order to provide adequate nutrition.

The present inventions fat mixtures possess adequate levels of phospholipids and an adequate relationship between oleic acid, linoleic acid and α-linolenic acid as well as adequate levels of long chain polyunsaturated fatty acids of both the n6 and n3 series. In addition, the fat mixtures of the present invention possess an adequate ratio of arachidonic acid (20:4n6) to docosahexaenoic acid (22:6n3). These fat mixtures are modeled on the fat content of human milk for infant diets and on the mediterranean diet for adult nutritional products. These diets promote the growth and development of the infant and contribute to the prevention and treatment of some diseases in adults.

DETAILED DESCRIPTION OF THE INVENTION

Human milk contains about 4 g/dl of lipids made up of the following components: 98% are triglycerides, 0.8% are phospholipids and 0.3% are cholesterol. Human milk generally contains the following amounts and types of fatty acids. The oleic acid (18:1n9) content of human milk ranges between 30–40%. Palmitic acid (16:0) is present from 20 to 25%. Stearic acid (18:0) makes up 5 to 7% of the fatty acids and myristic acid makes up about 4–7% of the fatty acids. The linoleic acid content normally varies between 6–16% and α-linolenic acid content varies between 1.2–1.3% of total fatty acid content.

The average composition of the fatty acids in human milk (Spanish mothers) and the approximate percentage intervals of the fatty acids of primary interest for control in the present invention are shown in Table 1.

TABLE 1

Fatty Acid Composition Of Human Milk

| Fatty Acid | Mean Amounts +/- SEM* | Approximate % Intervals |
|---|---|---|
| 10:0 | 1.78 ± 0.16 | |
| 12:0 | 7.15 ± 0.36 | |
| 14:0 | 6.48 ± 0.31 | |
| 15:0 | — | |
| 16:0 | 16.96 ± 0.31 | |
| 16:1n7 | 3.21 ± 0.12 | |
| 17:0 | — | |
| 18:0 | 4.80 ± 0.16 | |
| 18:1n9 | 40.14 ± 0.90 | 30–45 |
| 18:2n6 | 16.07 ± 0.71 | 6–20 |
| 18:3n3 | 1.36 ± 0.10 | 0.3–1.8 |
| 20:0 | — | |
| 20:2n6 | 0.50 ± 0.71 | |
| 20:3n6 | 0.68 ± 0.71 | |
| 20:4n6 | 0.66 ± 0.71 | 0.1–1 |
| 20:5n3 | 0.21 ± 0.10 | |
| 21:0 | — | |
| 22:4n6 | 0.1 ± 0.10 | |
| 22:5n6 | — | |
| 22:5n3 | 0.25 ± 0.10 | |
| 22:6n3 | 0.40 ± 0.10 | 0.1–1 |

*SEM = Means Standard Error

Human milk contains both medium chain, a well as long chain fatty acids, and is especially rich in PUFA of the n6 and n3 series. All of theses acids are particularly abundant in the milk of mothers with premature children.

Human milk also contains long chain PUFAs, of both the n6 and n3 series. The total amount of these acids is normally about 2% of the total amount of fatty acids present in human milk. Of these long chain acids, arachidonic acid (20:4n6), docosahexaenoic acid (22:6n3) and eicosatrienoic acid (20:3n6) are the predominant long chain PUFAs.

As indicated previously, the ratio of oleic acid (18:1n9) to linoleic acid (18:2n6) to α-linolenic acid (18:3n3) is a regulating factor in the synthesis of long chain PUFAs and eicosanoids. The numerical value of this ratio in human milk is in the range of 30–45:6–20:0.3–1.8.

Another important long chain polyunsaturated fatty acid ratio in the diet, is the ratio of arachidonic acid (20:4n6) to docosahexaenoic acid (22:6n3). This is due to the importance of docosahexaenoic acid (22:6n3) as a component of the membrane lipids in both the cerebrum and retina. In human milk, this ratio is in the range of approximately 0.1–1:0.1–1.

With regards to adult nutrition, the diet of mediterranean countries is currently considered a good model due to the low incidence in these countries of diseases, such as, cardiovascular disease, atherosclerosis and cancer.

The approximate fatty acid composition in the standard mediterranean diet and the approximate intervals of the calculated percentages for the fatty acids of primary interest for intervention in the present invention are shown in Table 2.

TABLE 2

Average Analysis Of Fatty Acids In The Mediterranean Diet (g/100 g Of Total Fatty Acids)

| Fatty Acid | Mean Content | Approximate % Intervals |
|---|---|---|
| 14:0 | 0.6 | |
| 16:0 | 19.2 | |
| 16:1 | 0.4 | |
| 18:0 | 6.4 | |
| 18:1 | 58.1 | 30–80 |
| 18:2n6 linoleic acid | 12.0 | 3–18 |
| 18:3n3 α-linolenic acid | 0.9 | 0.3–3 |
| 20:4n6 arachidonic | 0.1 | 0.1–2 |
| 20:5n3 eicosapentaenoic acid | 0.6 | |
| 22:6n3 docosahexaenoic acid | 0.6 | 0.1–3 |

The ratio of oleic acid (18:1n9) to linoleic acid (18:2n6) to α-linolenic acid (18:3n3) in the mediterranean diet is in the range 30–80:3–20:0.3–3. For the long chain polyunsaturated fatty acids, the ratio of arachidonic acid (20:4n6) to docosahexaenoic acid (22:6n3) is in the range of 0.1–2:0.1–3.

The present invention is a new fat mixture which provides adequate levels of phospholipids and an adequate ratio of oleic, linoleic and α-linolenic acids, as well as sufficient levels of long-chain PUFAs, both series n6 and series n3. In addition, the fat mixtures in this invention provide an adequate ratio of arachidonic acid (20:4n6) to docosahexaenoic acid (22:6n3). These fat mixtures follow the model of fat content in human milk for infant formulas, and the so-called "Mediterranean diet" for adult food products. These diets support the growth and development of children and contribute to improved nutrition, as well as the prevention and treatment of certain diseases in adults.

For diets intended for patients with specific pathologies, it would be desirable to supplement the diet with long chain PUFAs. For example, for cardiovascular patients, it would be convenient to supply the diet with long chain PUFAs of the n3 series, specifically with eicosapentaenoic acid 20:5n3. Where cirrhosis is the problem, the diet should be supplied with long chain PUFAs of both the n3 and n6 series.

Taking into account the importance of PUFAs as a structural component of membrane phospholipids, and since long chain PUFAs which are precursors's of eicosanoids are obtained from these phospholipids by the action of phospholipids, it would be desirable to associate the PUFAs with the phospholipids. In human milk phospholipids are present in a concentration ranging from 23.8–81.5 mg/dl, equivalent to 0.7–8% of total lipids. There are different components, of the phospholipids which are present in the following amounts. Phosphatidyl choline 28–29%, phosphatidyl ethanolamine 26–27%, sphingomyelins 30–32%, phosphatidyl serine 5–6% and phosphatidyl inositol 4–5%.

Since the majority of polyunsaturated fatty acids in human milk are associated with phospholipids, it follows that polyunsaturated fatty acids in artificial formulas should be associated with phospholipids.

It has been demonstrated that milk phospholipids can protect the gastric mucosa, as they mediate the cytoprotective effects of prostaglandins.

A preferred source of phospholipids for the present invention is animal brain material. Table 3 shows the approximate fatty acid composition of calf and pig brain material, and provides a comparison with the fatty acid composition of other sources of PUFAs, for example, egg yolks, according to U.S. Pat. No. 4,670,285 and German Patent DE 3,603,000, and placentas according to French Patent 2,553,621.

TABLE 3

Fatty Acid Composition of Different PUFA Biological Sources

| | Calf[1] Brain | Pig[1] Brain | Egg[2] Yolk | Placenta |
|---|---|---|---|---|
| 14:0 | 4.1 | — | — | 0.6 |
| 16:0 | 17.2 | 15.3 | 26.1 | 30.0 |
| 16:1 | 1.8 | 0.8 | 3.3 | 1.5 |
| 18:0 | 16.3 | 17.5 | 10.2 | 13.0 |
| 18:1 | 29.0 | 29.5 | 37.1 | 12.1 |
| 18:2n6 | 0.5 | 1.0 | 10.7 | 8.8 |
| 18:3n3 | 0.8 | 0.6 | 0.3 | — |
| 18:3n6 | 0.1 | 0.3 | — | — |
| 20:2n6 | 0.6 | 0.6 | — | 0.8 |
| 20:3n6 | 0.7 | 0.9 | — | 4.0 |
| 20:4n6 | 8.9 | 11.4 | 1.5–2.8 | 16.0 |
| 20:5n3 | 0.5 | 0.3 | 0–0.1 | 0.1 |
| 22:4n6 | 5.1 | 4.8 | 0.2–0.3 | 1.2 |
| 24:0 | 2.2 | 3.5 | — | 1.1 |
| 24:1 ± 22:5n6 | 1.9 | 3.9 | — | — |
| 22:5n30.3 | 0.3 | 0.1 | 0.2–0.4 | 1.6 |
| 22:6n3 | 8.1 | 8.7 | 0.5–0.9 | 2.2 |

[1]This patent
[2]U.S Pat. No. 4.670.285), DE-3,603,000
[3]French Patent, 2.553.261

A primary objective of the present invention is to provide a fat mixture which contains adequate ratios of oleic acid (18:1n9) to linoleic acid (18:2n6) to α-linolenic acid (18:3n3). The fat mixture should also contain adequate levels and ratios of the long chain PUFAs of the n3 and n6 series, especially the ratio of 20:4n6 to 22:6n3. These controlled ratios are desirable to promote adequate growth and development to nursing infants, either term or pre-term, and to prevent and treat certain diseases in adults.

Another objective is to provide a nutritional product containing an adequate level of phospholipids, particularly those obtained from pig or calf brains, or the brains of other domestic animals.

Another objective is to provide nutritional products rich in PUFAs of both the n6 and n3 series, independent from the ratios 18:1n9/18:2n6/18:3n3, which are useful for the dietetic treatment of some illnesses in adults.

Another objective of the present invention is to provide formulas for the feeding of very low birth weight, newborn, infants, term infants, and to provide lactose-free formulas and hydrolyzed protein lactose-free formulas which possess a composition of phospholipids and fatty acids which is similar to that of human milk.

Another objective of the present invention is to provide a variety of formulas for adult nutrition, where the diet consists of a specific composition of fatty acids and phospholipids. These diets can be administered by either oral or enteral methods.

Another objective of the present invention is to provide diverse nutritional products rich in PUFAs, for the dietetic treatment of some illnesses, such as hepatic cirrhosis.

Another objective of the present invention is to provide a mixture of added fat from a mixture of nucleosides and/or nucleotides: uridine and/or uridine monophosphate, guanosine and/or guanosine monophosphate, adenosine and/or adenosine monophosphate, cytidine and/or cytidine monophosphate and inosine and/or inosine monophosphate. This embodiment may be used as a specific product or as an additive to another nutritional product, for example milk, which forms this part of a diet.

This mixture of added fat of nucleotides and/or nucleosides, has been shown to be particularly effective in the treatment of infant diarrhea. This mixture controls the incidence as well as in its duration of the diarrhea. These mixture also demonstrate the restoring effects towards the intestinal wall.

In experiments conducted with 193 children during a 3 month period, to those that were administered a milk with additions of the fatty mixture with the nucleotides and/or nucleosides mentioned above (Milk I) showed the following results when compared to children that were administered conventional milk (Milk II).

| | Milk I | Milk II |
|---|---|---|
| Number of Children evaluated | 89 | 84 |
| Episodes of diarrhea | 38 | 54 |
| incidence (%) | 42.7 | 64.3 |

In addition, in the experiment conducted above, a significant reduction in the duration of the diarrheic episodes was observed.

| | Milk I | Milk II |
|---|---|---|
| Average Duration (days) | 6.26 | 8.29 |
| Total days with diarrhea | 219 | 398 |
| Ten day episodes | 6 (17.1%) | 13 (27.1%) |

According to the invention, a preferred fat mixture is a mixture of brain phospholipids from domestic animals, preferably a calf or a pig, and at least one oil of the group of olive oil, soybean oil, corn oil, coconut oil and palm oil and/or at least one or more oils selected from animal milk fat (a dairy product or lard), a fish oil, and medium chain triglycerides obtained from refining vegetable oils.

TABLE 4

Products for Infant Nutrition
Composition of Fatty Materials

| | % of fat in mixture | | | | | |
|---|---|---|---|---|---|---|
| | a | b | a | b | a | b |
| Examples | 1 | | 2 | | 3 | |
| % of fat/100 g of product | 28 | | 29 | | 21.3 | |
| Olive oil | 43 | 43 | 10.5 | 10.5 | 10.5 | 10.5 |
| Soybean oil | 14.3 | 14.3 | 10.5 | 10.5 | 10.5 | 10.5 |
| Milkfat | 23.9 | 23.9 | 49.7 | 49.7 | 49.7 | 49.7 |
| MCT | 14.3 | 14.3 | 4.8 | 4.8 | 4.8 | 4.8 |
| Brain phospholipids | 4.5 | 3.2 | 4.5 | 3.4 | 4.5 | 3.0 |
| Fish oil | — | 1.3 | — | 1.1 | — | 1.5 |
| Examples | 4 | | 5 | | 6 | |
| % of fat/100 g of product | 22.9 | | 23 | | 22 | |
| Olive oil | 30.5 | 30.5 | 30.5 | 30.5 | 30.5 | 39.1 |
| Soybean oil | 10.5 | 10.5 | 10.5 | 10.5 | 13.4 | 13.4 |
| Milkfat | 49.7 | 49.7 | 49.7 | 49.7 | 19.1 | 19.1 |
| MCT | 4.8 | 4.8 | 4.8 | 4.8 | 23.9 | 23.9 |
| Brain phospholipids | 4.5 | 2.0 | 4.5 | 1.5 | 4.5 | 1.0 |
| Fish oil | — | 2.5 | — | 3.0 | — | 3.5 |

TABLE 5

Products for Adult Nutrition: Fat Composition

| | Example No. | | | | | | | |
|---|---|---|---|---|---|---|---|---|
| | 7 | | 8 | | 9 | | 10 | |
| g of fat/100 g of product | 22 | | 16.6 | | 16.6 | | 7.7 | |
| % of fats in the mixture | a | b | a | b | a | b | a | b |
| Olive oil | 33.4 | 33.4 | 33.4 | 33.4 | 36.3 | 36.3 | — | — |
| Soy oil | 11.5 | 11.5 | 11.5 | 11.5 | 12.4 | 12.4 | — | — |
| Corn oil | — | — | — | — | — | — | 36.3 | 36.3 |
| Milkfat | 41.4 | 41.4 | 41.1 | 41.1 | 18.1 | 18.1 | — | — |
| MCT | 9.5 | 9.5 | 9.5 | 9.5 | 28.7 | 28.7 | 59.2 | 59.2 |
| Brain phospholipids | 4.5 | 2.4 | 4.5 | 2.1 | 4.5 | 1.9 | 4.5 | 2.6 |
| Fish oil | — | 2.1 | — | 2.4 | — | 2.6 | — | 1.9 |

TABLE 6

Fatty Acid Composition of Infant Nutrition Products (g/100 g Total Fat)

| | Example No. | | | | | |
|---|---|---|---|---|---|---|
| | 1 | | 2 | | 3 | |
| | a | b | a | b | a | b |
| 8:0 | 7.20 | 7.20 | 2.40 | 2.39 | 2.35 | 2.35 |
| 10:0 | 8.90 | 8.90 | 3.80 | 3.72 | 3.70 | 3.70 |
| 12:0 | 1.20 | 1.20 | 1.90 | 1.91 | 1.80 | 1.80 |
| 14:0 | 3.10 | 3.07 | 5.20 | 2.11 | 5.00 | 4.06 |
| 16:0 | 15.05 | 15.45 | 18.80 | 18.67 | 19.00 | 19.40 |
| 16:1n7 | 1.60 | 1.67 | 1.70 | 1.75 | 1.60 | 1.68 |
| 18:0 | 5.40 | 5.08 | 8.03 | 7.58 | 7.90 | 7.53 |
| 18:1n9 | 39.20 | 39.14 | 39.70 | 39.05 | 39.80 | 39.73 |
| 18:2n6 | 14.50 | 14.52 | 13.80 | 13.27 | 13.85 | 13.87 |
| 18:3n3 | 1.30 | 1.30 | 1.10 | 1.10 | 1.10 | 1.10 |
| 20:1 + 18:4n3 | 0.07 | 0.10 | 0.07 | 0.09 | 0.07 | 0.10 |
| 20:2n6 | 0.03 | 0.02 | 0.03 | 0.02 | 0.03 | 0.04 |
| 20:3n6 | 0.03 | 0.03 | 0.03 | 0.03 | 0.03 | 0.03 |
| 20:4n6 | 0.40 | 0.29 | 0.40 | 0.30 | 0.40 | 0.27 |
| 20:5n3 | 0.03 | 0.14 | 0.03 | 0.12 | 0.03 | 0.16 |
| 22:4n6 | 0.23 | 0.16 | 0.23 | 0.17 | 0.23 | 0.15 |

TABLE 6-continued

Fatty Acid Composition of Infant Nutrition Products (g/100 g Total Fat)

| | Example No. | | | | | |
|---|---|---|---|---|---|---|
| | 1 | | 2 | | 3 | |
| | a | b | a | b | a | b |
| 24:0 | 0.10 | 0.08 | 0.10 | 0.08 | 0.10 | 0.08 |
| 24:1 + 22:5n6 | 0.10 | 0.08 | 0.10 | 0.08 | 0.10 | 0.08 |
| 22:5n3 | 0.02 | 0.03 | 0.02 | 0.03 | 0.02 | 0.03 |
| 22:6n3 | 0.36 | 0.42 | 0.36 | 0.41 | 0.36 | 0.43 |

Ratio (18:1n9):(18:2n6):(18:3n3)

Example 1-a = 30:11.1:1; b = 30.1:11.2:1
Example 2-a = 36:12.5:1; b = 35.5:12.0:1
Example 3-a = 36:12.5:1 b = 36.1:12.6:1

Ratio (20:4n6):(22:6n3)

Example 1-a = 1.11:1; b = 0.69:1
Example 2-a = 1.11:1; b = 0.73:1
Example 3-a = 1.11:1; b = 0.63:1

TABLE 7

Fatty Acid Composition of Infant Nutrition Products (g/100 of Total Fat)

| | Example No. | | | | | |
|---|---|---|---|---|---|---|
| | 4 | | 5 | | 6 | |
| | a | b | a | b | a | b |
| 8:0 | 2.50 | 2.38 | 2.40 | 2.38 | 9.50 | 9.45 |
| 10:0 | 3.60 | 3.72 | 3.70 | 3.72 | 14.00 | 13.94 |
| 12:0 | 1.90 | 1.91 | 1.90 | 2.00 | 1.30 | 1.33 |
| 14:0 | 5.10 | 5.18 | 5.10 | 5.18 | 2.10 | 2.13 |
| 16:0 | 18.90 | 18.73 | 19.00 | 18.74 | 12.50 | 12.66 |
| 18:1n7 | 1.70 | 1.81 | 1.70 | 1.36 | 1.30 | 1.38 |
| 18:0 | 8.15 | 7.42 | 8.10 | 7.37 | 4.40 | 3.97 |
| 18:1n9 | 39.60 | 39.16 | 39.70 | 39.13 | 35.80 | 35.56 |
| 18:2n6 | 13.82 | 13.35 | 13.75 | 13.38 | 14.30 | 14.46 |
| 18:3n3 | 1.10 | 1.05 | 1.10 | 1.11 | 1.30 | 1.31 |
| 20:1 + 18:4n3 | 0.07 | 0.13 | 0.07 | 0.14 | 0.07 | 0.14 |
| 20:2n6 | 0.03 | 0.01 | 0.03 | 0.01 | 0.03 | 0.01 |
| 20:3n6 | 0.03 | 0.03 | 0.03 | 0.03 | 0.03 | 0.03 |
| 20:4n6 | 0.40 | 0.18 | 0.40 | 0.13 | 0.40 | 0.09 |
| 20:5n3 | 0.03 | 0.25 | 0.03 | 0.29 | 0.03 | 0.34 |
| 22:4n6 | 0.23 | 0.10 | 0.23 | 0.08 | 0.23 | 0.05 |

TABLE 7-continued

Fatty Acid Composition of Infant Nutrition Products (g/100 of Total Fat)

| | Example No. | | | | | |
|---|---|---|---|---|---|---|
| | 4 | | 5 | | 6 | |
| | a | b | a | b | a | b |
| 24:0 | 0.10 | 0.04 | 0.10 | 0.03 | 0.10 | 0.02 |
| 24:1 + 22:5n6 | 0.10 | 0.04 | 0.10 | 0.03 | 0.10 | 0.02 |
| 22:5n3 | 0.02 | 0.04 | 0.02 | 0.04 | 0.02 | 0.05 |
| 22:6n3 | 0.36 | 0.47 | 0.36 | 0.49 | 0.36 | 0.51 |

Ratio (18:1n9):(18:2n6):(18:3n3)

Example 4-a = 36:12.5:1; b = 37.3:12.7:1
Example 5-a = 36:12.5:1; b = 35.2:12.0:1
Example 6-a = 27.5:11.1:1; b = 27.1:11:1

Ratio (20:4n6):(22:6n3)

Example 4-a = 1.1:1; b = 0.38:1
Example 5-a = 1.1:1; b = 0.26:1
Example 6-a = 1.1:1; b = 0.18:1

TABLE 8

Fatty Acid Composition of Adult Nutrition Products (g/100 g Total Fat)

| | Example No. | | | | | | | |
|---|---|---|---|---|---|---|---|---|
| | 7 | | 8 | | 9 | | 10 | |
| | a | b | a | b | a | b | a | b |
| 6:0 | 0.10 | 0.10 | 0.10 | 0.10 | 0.3 | 0.10 | 0.60 | 0.60 |
| 8:0 | 4.20 | 4.20 | 4.20 | 4.10 | 11.25 | 10.94 | 22.30 | 21.29 |
| 10:0 | 6.30 | 6.30 | 6.20 | 6.20 | 16.50 | 16.30 | 32.96 | 31.47 |
| 12:0 | 1.70 | 1.70 | 1.60 | 1.60 | 1.50 | 1.40 | 1.75 | 1.70 |
| 14:0 | 4.70 | 4.56 | 4.70 | 4.70 | 2.20 | 2.10 | 0.18 | 0.18 |
| 16:0 | 17.60 | 17.86 | 17.70 | 17.68 | 11.90 | 11.91 | 4.75 | 4.75 |
| 16:1 | 1.60 | 1.72 | 1.60 | 1.79 | 1.15 | 1.36 | 0.10 | 0.26 |
| 18:0 | 6.90 | 6.65 | 7.10 | 6.61 | 4.10 | 3.80 | 2.15 | 2.18 |
| 18:1 | 39.20 | 38.92 | 39.40 | 39.10 | 33.30 | 33.00 | 10.15 | 10.25 |
| 18:2n6 | 12.64 | 12.11 | 12.75 | 12.11 | 12.70 | 12.64 | 18.06 | 17.22 |
| 18:3n3 | 1.20 | 1.21 | 1.10 | 1.21 | 1.20 | 1.22 | 3.20 | 3.21 |
| 20:1 + 18:4n3 | 0.07 | 0.10 | 0.07 | 0.10 | 0.07 | 0.03 | 0.07 | 0.03 |
| 20:2n6 | 0.03 | 0.01 | 0.03 | 0.01 | 0.03 | 0.01 | 0.03 | 0.01 |
| 20:3n6 | 0.03 | 0.01 | 0.03 | 0.01 | 0.03 | 0.01 | 0.03 | 0.01 |
| 20:4n6 | 0.40 | 0.24 | 0.40 | 0.22 | 0.40 | 0.20 | 0.40 | 0.25 |
| 20:5n3 | 0.03 | 0.22 | 0.03 | 0.25 | 0.03 | 0.27 | 0.03 | 0.20 |
| 22:4n6 | 0.23 | 0.16 | 0.23 | 0.15 | 0.23 | 0.14 | 0.23 | 0.27 |
| 24:0 | 0.10 | 0.03 | 0.10 | 0.03 | 0.10 | 0.02 | 0.10 | 0.03 |
| 24:1 + 22:5n6 | 0.10 | 0.03 | 0.10 | 0.03 | 0.10 | 0.02 | 0.10 | 0.03 |
| 22:5n3 | 0.02 | 0.02 | 0.02 | 0.05 | 0.02 | 0.06 | 0.02 | 0.04 |
| 22:6n3 | 0.36 | 0.45 | 0.36 | 0.46 | 0.36 | 0.47 | 0.36 | 0.48 |

Ratio 18:1n9/18:2n6/18:3n3

Example No. 7-a = 32.7:10.6:1; b = 32.2:10:1
Example No. 8-a = 35.8:11.6:1; b = 32.3:10:1
Example No. 9-a = 27.8:10.6:1; b = 27.0:10.4:1
Example No. 10-a = 3.2:5.6:1; b = 3.2:5.4:1

Ratio 20:4n6/22:6n3

Example No. 7-a = 1.1:1; b = 0.53:1
Example No. 8-a = 1.1:1; b = 0.48:1
Example No. 9-a = 1.1:1; b = 0.42:1
Example No. 10-a = 1.1:1; b = 0.52:1

TABLE 9

Fatty Acid Composition of Infant Nutrition Products (g/100 g Product)

| | Example No. | | | | | |
|---|---|---|---|---|---|---|
| | 1 | | 2 | | 3 | |
| | a | b | a | b | a | b |
| 8:0 | 1.714 | 1.714 | 0.592 | 0.589 | 0.434 | 0.434 |
| 10:0 | 2.118 | 2.118 | 0.937 | 0.918 | 0.688 | 0.688 |
| 12:0 | 0.286 | 0.286 | 0.468 | 0.471 | 0.344 | 0.344 |
| 14:0 | 0.740 | 0.731 | 1.282 | 0.520 | 0.941 | 0.764 |
| 16:0 | 3.570 | 3.68 | 4.634 | 4.605 | 3.404 | 3.476 |
| 16:1n7 | 0.381 | 0.397 | 0.419 | 0.432 | 0.308 | 0.323 |
| 17:0 | — | — | — | — | — | — |
| 18:0 | 1.285 | 1.210 | 1.972 | 1.870 | 1.448 | 1.380 |
| 18:1n9 | 9.330 | 9.317 | 9.786 | 9.632 | 7.189 | 7.175 |
| 18:2n6 | 3.451 | 3.457 | 3.402 | 3.273 | 2.498 | 2.502 |
| 18:3n3 | 0.309 | 0.309 | 0.271 | 0.271 | 0.199 | 0.199 |
| 20:1 + 18:4n3 | 0.017 | 0.024 | 0.017 | 0.022 | 0.013 | 0.018 |
| 20:2n6 | 0.007 | 0.005 | 0.007 | 0.005 | 0.005 | 0.006 |
| 20:3n6 | 0.007 | 0.007 | 0.007 | 0.007 | 0.005 | 0.005 |
| 20:4n6 | 0.095 | 0.069 | 0.099 | 0.074 | 0.072 | 0.049 |
| 20:5n3 | 0.007 | 0.033 | 0.007 | 0.029 | 0.005 | 0.026 |
| 22:4n6 | 0.055 | 0.038 | 0.057 | 0.042 | 0.041 | 0.027 |
| 24:0 | 0.024 | 0.019 | 0.025 | 0.020 | 0.018 | 0.014 |
| 24:1 + 22:5n6 | 0.024 | 0.019 | 0.025 | 0.020 | 0.018 | 0.014 |
| 22:5n3 | 0.005 | 0.007 | 0.005 | 0.007 | 0.004 | 0.006 |
| 22:6n3 | 0.086 | 0.100 | 0.089 | 0.101 | 0.065 | 0.078 |

TABLE 10

Fatty Acid Composition of Infant Nutrition Products (g/100 g Product)

| | Example No. | | | | | |
|---|---|---|---|---|---|---|
| | 4 | | 5 | | 6 | |
| | a | b | a | b | a | b |
| 8:0 | 0.469 | 0.446 | 0.469 | 0.467 | 0.776 | 1.767 |
| 10:0 | 0.743 | 0.698 | 0.743 | 0.727 | 2.618 | 2.606 |
| 12:0 | 0.371 | 0.358 | 0.371 | 0.391 | 0.243 | 0.249 |
| 1f1:0 | 1.017 | 0.971 | 1.017 | 1.012 | 0.393 | 0.398 |
| 16:0 | 3.675 | 3.514 | 3.675 | 3.662 | 2.337 | 2.367 |
| 16:1n7 | 0.332 | 0.340 | 0.332 | 0.265 | 0.243 | 0.258 |
| 17:0 | — | — | — | — | — | — |
| 18:0 | 1.564 | 1.391 | 1.564 | 1.440 | 0.823 | 0.742 |
| 18:1n9 | 7.761 | 7.346 | 7.761 | 7.647 | 6.695 | 6.648 |
| 18:2n6 | 2.698 | 2.504 | 2.698 | 2.615 | 2.674 | 2.703 |
| 18:3n3 | 0.215 | 0.197 | 0.215 | 0.217 | 0.243 | 0.245 |
| 20:1 + 18:4n3 | 0.014 | 0.024 | 0.014 | 0.027 | 0.013 | 0.026 |
| 20:2n6 | 0.006 | 0.002 | 0.006 | 0.002 | 0.006 | 0.002 |
| 20:3n6 | 0.006 | 0.006 | 0.006 | 0.006 | 0.006 | 0.006 |
| 20:4n6 | 0.078 | 0.034 | 0.078 | 0.025 | 0.080 | 0.017 |
| 20:5n3 | 0.006 | 0.047 | 0.006 | 0.057 | 0.006 | 0.063 |
| 22:4n6 | 0.045 | 0.019 | 0.045 | 0.016 | 0.043 | 0.009 |
| 24:0 | 0.019 | 0.007 | 0.019 | 0.006 | 0.019 | 0.004 |
| 24:1 + 22:5n6 | 0.019 | 0.007 | 0.019 | 0.006 | 0.019 | 0.004 |
| 22:5n3 | 0.003 | 0.007 | 0.003 | 0.008 | 0.004 | 0.009 |
| 22:6n3 | 0.070 | 0.088 | 0.070 | 0.096 | 0.007 | 0.095 |

TABLE 11

Fatty Acid Composition of Adult Nutrition Products (g/100 g of Product)

| | _____ Example No. _____ | | | | | | | |
|---|---|---|---|---|---|---|---|---|
| | 7 | | 8 | | 9 | | 10 | |
| | a | b | a | b | a | b | a | b |
| 6:0 | 0.019 | 0.019 | 0.014 | 0.014 | 0.042 | 0.014 | 0.039 | 0.039 |
| 8:0 | 0.785 | 0.785 | 0.593 | 0.593 | 1.587 | 1.543 | 1.459 | 1.393 |
| 10:0 | 1.178 | 1.178 | 0.889 | 0.889 | 2.328 | 2.300 | 2.153 | 2.059 |
| 12:0 | 0.318 | 0.318 | 0.240 | 0.240 | 0.212 | 0.197 | 0.114 | 0.046 |
| 14:0 | 0.879 | 0.853 | 0.663 | 0.659 | 0.310 | 0.296 | 0.012 | 0.012 |
| 16:0 | 3.291 | 3.333 | 2.483 | 2.481 | 1.679 | 1.680 | 0.311 | 0.311 |
| 16:1 | 0.299 | 0.322 | 0.226 | 0.251 | 0.162 | 0.192 | 0.006 | 0.017 |
| 18:0 | 1.290 | 1.243 | 0.974 | 0.987 | 0.578 | 0.536 | 0.141 | 0.142 |
| 18:1 | 7.330 | 7.277 | 5.531 | 5.489 | 4.699 | 4.655 | 0.664 | 0.629 |
| 18:2n6 | 2.364 | 2.265 | 1.783 | 1.700 | 1.791 | 1.783 | 1.182 | 1.057 |
| 18:3n3 | 0.224 | 0.226 | 0.169 | 0.169 | 0.169 | 0.171 | 0.209 | 0.197 |
| 20:1 + 18:4 | 0.013 | 0.019 | 0.010 | 0.014 | 0.010 | 0.003 | 0.005 | 0.002 |
| 20:2n6 | 0.006 | 0.001 | 0.004 | 0.001 | 0.004 | 0.001 | 0.002 | 0.001 |
| 20:3n6 | 0.006 | 0.001 | 0.004 | 0.001 | 0.004 | 0.001 | 0.002 | 0.001 |
| 20:4n6 | 0.075 | 0.037 | 0.056 | 0.027 | 0.056 | 0.025 | 0.026 | 0.002 |
| 20:5n3 | 0.006 | 0.041 | 0.004 | 0.030 | 0.004 | 0.033 | 0.002 | 0.012 |
| 22:4n6 | 0.043 | 0.030 | 0.032 | 0.018 | 0.032 | 0.017 | 0.015 | 0.010 |
| 24:0 | 0.019 | 0.006 | 0.014 | 0.004 | 0.014 | 0.003 | 0.006 | 0.002 |
| 24:1 + 22:5n6 | 0.019 | 0.006 | 0.014 | 0.004 | 0.014 | 0.003 | 0.006 | 0.002 |
| 22:5n3 | 0.004 | 0.009 | 0.003 | 0.006 | 0.003 | 0.007 | 0.001 | 0.002 |
| 22:6n3 | 0.067 | 0.084 | 0.050 | 0.057 | 0.050 | 0.058 | 0.023 | 0.029 |

Preferably, the content of brain phospholipids in the fat mixture should be in the range 2–25 g per 100 g the mixture. A preferred embodiment of the present fat mixture is one derived from the mixture of phospholipids from brain and milk fat, medium chain triglycerides (MCT), olive oil and soy oil in the proportions shown in Table 4 and 5. Table 4 shows the examples of infant nutrition products (Examples 1 to 6). For adult nutrition, the preferred mixture contains brain phospholipids, milk fat, medium chain triglycerides, olive oil, corn oil, soy oil and fish oil in the proportions shown in table 5 (Examples 7 to 10).

The fat mixture of the present invention is exemplified in Examples 1 to 10 of the present application. Dietary compositions utilizing these fat mixtures are disclosed in Examples 11 to 21. Tables 6 to 11 show the fatty acid composition of the particular fat mixtures shown in the examples. Tables 6 to 8 disclose the relative amounts of each fatty acid relative to the total amount of fatty acids. Tables 9 to 11 disclose the relative amounts of each fatty acid per 100 grams of dietary product.

Each of these examples discloses the fatty acid composition of the fat mixture as well as the ratio of oleic acid (18:1n9) to linoleic acid (18:2n6) to α-linolenic acid (18:3n3) and the ratio between arachidonic acid (20:4n6) and docosahexaenoic acid (22:6n3) (Tables 6 to 8).

The fatty acid profile in the products for infant nutrition, according to the present invention, is similar to the fatty acid profile for human milk. The fatty acid profile for adult nutrition compositions of the present invention is similar to that of the mediterranean diet. In addition, the present fat mixture has a low content of lauric and myristic acid. The stearic acid content is less than 10% of the fatty acid total and the of the palmitic acid content is less than 20% of the fatty acid content. A higher content of these fatty acids could produce clots, which would inhibit the absorption of fats.

With respect to the amount of oleic acid (18:1n9), the energy it provides in the products ranges from 15–20% of the total energy. The amount of energy supplied by the essential fatty acids, linoleic and α-linolenic acid, ranges between 3–8% and 0.4–0.5% of the total energy respectively.

The mixtures of the present invention possess values for the ratio of oleic acid (18:1n9) to linoleic acid (18:2n6) to α-linolenic acid (18:3n3) in the range 30–45:6–20:0.3–1.8 for the infant formulas and in the range 30–80:3–20:0.3–3 for the adult nutrition formulas.

The long chain PUFAs content of the fat mixtures of the present invention is approximately 0.40% for arachidonic acid 20:4n6, and about 0.3%–0.4% of the total fatty acids for docosahexaenoic acid (22:6n3). The ratio of arachidonic acid (20:4n6) to docosahexaenoic acid (22:6n3) in the fat mixture varies in the range 0.1–2:0.1–3. A preferred ratio range is 0.1–1:0.1–1. The amount of eicosapentaenoic acid (20:5n3) is not greater than 0.03% of the total fatty acids in the products for infant nutrition.

The ratio of oleic acid (18:1n9) to linoleic acid (18:2n6) to α-linolenic acid (18:3n3) and of arachidonic acid (20:4n6) to docosahexaenoic acid (22:6n3) are also similar to those found the model diets (human milk and mediterranean diet). With regards to the biological source of the PUFAs used in this invention (pig or calf brain or from other domestic animals), the long chain PUFAs are associated with the phospholipids. Phospholipids represent approximately 70% of the lipids from the brains, the remaining 30% corresponding to cerebrosides, sulfatides and cholesterol (2.2 g %). The fact that the long chain PUFAs are associated to phospholipids presents an advantage, especially when it is considered that long chain PUFAs in tissues are structural components of membrane phospholipids.

The following Examples illustrate nutritional products and fat mixtures of the present invention. They are not intended to limit the present invention, those skilled in the art can make their own interpretation of the following examples.

EXAMPLE 1

A fat mixture for use in an infant nutritional product which contains 28 grams of fat per 100 grams of product. The fat mixture is made up of the following compounds in the designated amounts:

| | a | b |
|---|---|---|
| Olive Oil | 43.0% | 43.0% |
| Soy Oil | 14.3% | 14.3% |
| Milkfat | 23.9% | 23.9% |
| MCT | 14.3% | 14.3% |
| Brain phospholipids | 4.5% | 3.2% |
| Fish Oil | — | 1.3% |

Fat mixture 1a has an Oleic Acid:Linoleic Acid:α-Linolenic Acid ratio of 30:11.1:1 and a arachidonic acid:docosahexaenoic acid ratio of 1.11:1. Fat mixture 1b has an Oleic Acid:Linoleic acid: α-Linolenic acid ratio of 30.1:11.2:1 and an arachidonic acid:docosahexaenoic acid ratio of 0.69:1.

EXAMPLE 2

A fat mixture for use in an infant nutritional product which contains 29 grams of fat per 100 grams of product. The fat mixture is made up of the following compounds in the designated amounts:

|  | a | b |
|---|---|---|
| Fish Oil | — | 1.1% |
| Olive Oil | 30.5% | 30.5% |
| Soy Oil | 10.5% | 10.5% |
| Milkfat | 49.7% | 49.7% |
| MCT | 4.8% | 4.8% |
| Brain phospholipids | 4.5% | 3.4% |

Fat mixture 2a has an Oleic Acid:Linoleic Acid:α-Linolenic Acid ratio of 36:12.5:1 and a arachidonic acid:docosahexaenoic acid ratio of 1.11:1. Fat mixture 2b has a Oleic Acid:Linoleic Acid:α-Linolenic Acid ratio of 35.5:12:1 and arachidonic acid:docosahexaenoic acid ratio of 0.73:1

EXAMPLE 3

A fat mixture for use in an infant nutritional product which contains 21.3 grams of fat per 100 grams of product. The fat mixture is made up of the following compounds in the designated amounts:

|  | a | b |
|---|---|---|
| Olive Oil | 30.5% | 30.5% |
| Soy Oil | 10.5% | 10.5% |
| Milkfat | 49.7% | 49.7% |
| MCT | 4.8% | 4.8% |
| Brain phospholipids | 4.5% | 3.0% |
| Fish Oil | — | 1.5% |

Fat mixture 3a has an Oleic Acid:Linoleic Acid:α-Linolenic Acid ratio of 36:12.5:1 and a arachidonic acid:docosahexaenoic acid ratio of 1.11:1. Fat mixture 3b has an Oleic Acid:Linoleic Acid:α-Linolenic Acid ratios of 36.1:12.6:1 and an arachidonic acid:docosahexaenoic acid ratio of 0.63:1.

EXAMPLE 4

A fat mixture for use in an infant nutritional product which contains 22.9 grams of fat per 100 grams of product. The fat mixture is made up of the following compounds in the designated amounts:

|  | a | b |
|---|---|---|
| Fish Oil | — | 2.5% |
| Olive Oil | 30.5% | 30.5% |
| Soy Oil | 10.5% | 10.5% |
| Milkfat | 49.7% | 49.7% |
| MCT | 4.8% | 4.8% |
| Brain phospholipids | 4.5% | 2.0% |

Fat mixture 4a has an Oleic Acid:Linoleic Acid:α-Linolenic Acid ratio of 36:12.5:1 and a arachidonic acid:docosahexaenoic acid ratio of 1.1:1. Fat mixture 4b has an Oleic Acid:Linoleic Acid: α-Linolenic Acid ratio of 37.3:12.7:1 and a arachidonic acid: docosahexaenoic ratio of 0.38:1.

EXAMPLE 5

A fat mixture for use in an infant nutritional product which contains 23.0 grams of fat per 100 grams of product. The fat mixture is made up of the following compounds in the designated amounts:

|  | a | b |
|---|---|---|
| Olive Oil | 30.5% | 30.5% |
| Soy Oil | 10.5% | 10.5% |
| Milkfat | 49.7% | 49.7% |
| MCT | 4.8% | 4.8% |
| Brain phospholipids | 4.5% | 1.5% |
| Fish Oil | — | 3.0% |

Fat mixture 5a has an Oleic Acid:Linoleic Acid:α-Linolenic Acid ratio of 36:12.5:1 and a arachidonic acid:docosahexaenoic acid ratio of 1.1:1. Fat mixture 5b has an Oleic Acid:Linoleic Acid: α-Linolenic Acid and a ratio of 35.2:12:1 and an arachidonic acid:docosahexaenoic acid ratio of 0.26:1.

EXAMPLE 6

A fat mixture for use in an infant nutritional product which contains 22.0 grams of fat per 100 grams of product. The fat mixture is made up of the following compounds in the designated amounts:

|  | a | b |
|---|---|---|
| Olive Oil | 39.1% | 39.1% |
| Soy Oil | 13.4% | 13.4% |
| Milkfat | 19.1% | 19.1% |
| MCT | 23.9% | 23.9% |
| Brain phospholipids | 4.5% | 1.0% |
| Fish Oil | — | 3.5% |

Fat mixture 6a has an Oleic Acid:Linoleic Acid:α-Linolenic Acid ratio of 27.5:11.1:1 and a arachidonic acid:docosahexaenoic acid ratio of 1.1:1. Fat mixture 6b has an Oleic Acid:Linoleic Acid: α-Linolenic Acid ratio of 27.1:11.0:1 and an arachidonic acid:docosahexaenoic acid ratio of 0.18:1.

EXAMPLE 7

A fat mixture for use in an adult nutritional product which contains 22.0 grams of fat per 100 grams of product. The fat mixture is made up of the following compounds in the designated amounts:

|  | a | b |
|---|---|---|
| Olive Oil | 33.4% | 33.4% |
| Soy Oil | 11.5% | 11.5% |
| Milkfat | 41.1% | 41.1% |
| MCT | 9.5% | 9.5% |
| Brain phospholipids | 4.5% | 2.4% |
| Fish Oil | — | 2.1% |

Fat mixture 7a has an Oleic Acid:Linoleic Acid:α-Linolenic Acid ratio of 32.7:10.6:1 and a arachidonic acid:docosahexaenoic acid ratio of 1.1:1. Fat mixture 7b has an Oleic Acid:Linoleic Acid: α-Linolenic Acid ratio of 32.2:10:1 and an arachidonic acid:docosahexaenoic acid ratio of 0.53:1.

EXAMPLE 8

A fat mixture for use in an adult nutritional product which contains 16.6 grams of fat per 100 grams of product. The fat mixture is made up of the following compounds in the designated amounts:

|  | a | b |
|---|---|---|
| Olive Oil | 33.4% | 33.4% |
| Soy Oil | 11.5% | 11.5% |
| Milkfat | 41.1% | 41.1% |
| MCT | 9.5% | 9.5% |
| Brain phospholipids | 4.5% | 2.1% |
| Fish Oil | — | 2.4% |

Fat mixture 8a has an Oleic Acid:Linoleic Acid:α-Linolenic Acid ratio of 35.8:11.6:1 and a arachidonic acid:docosahexaenoic acid ratio of 1.1:1. Fat mixture 8b has an Oleic Acid:Linoleic Acid: α-Linolenic Acid ratio of 32.3:10:1 and an arachidonic acid:docosahexaenoic acid ratio of 0.48:1.

EXAMPLE 9

A fat mixture for use in an adult nutritional product which contains 16.6 grams of fat per 100 grams of product. The fat mixture is made up of the following compounds in the designated amounts:

|  | a | b |
|---|---|---|
| Olive Oil | 36.3% | 36.3% |
| Soy Oil | 12.4% | 12.4% |
| Milkfat | 18.1% | 18.1% |
| MCT | 28.7% | 28.7% |
| Brain phospholipids | 4.5% | 1.9% |
| Fish Oil | — | 2.6% |

Fat mixture 9a has an Oleic Acid:Linoleic Acid:α-Linolenic Acid ratio of 27.8:10.6:1 and a arachidonic acid:docosahexaenoic acid ratio of 1.1:1. Fat mixture 9b has an Oleic Acid:Linoleic Acid: α-Linolenic Acid ratio of 27:10.4:1 and an arachidonic acid:docosahexaenoic acid ratio of 0.42:1.

EXAMPLE 10

A fat mixture for use in an adult nutritional product which contains 7.7 grams of fat per 100 grams of product. The fat mixture is made up of the following compounds in the designated amounts:

|  | a | b |
|---|---|---|
| Corn Oil | 36.3% | 36.3% |
| MCT | 59.2% | 59.2% |
| Brain phospholipids | 4.5% | 2.6% |
| Fish Oil | — | 1.9% |

Fat mixture 10a has an Oleic Acid:Linoleic Acid:α-Linolenic Acid ratio of 3.2:56:1 and a arachidonic acid:docosahexaenoic acid ratio of 1.1:1. Fat mixture 10b has an Oleic Acid:Linoleic Acid:α-Linolenic Acid ratio of 3.2:5.4:1 and an arachidonic acid:docosahexaenoic acid ratio of 0.52:1.

EXAMPLE 11

Example 11 is an adapted milk product for preterm infants which incorporates one of the fat mixtures of the present invention.

Example 11: Adapted Milk Formula for Preterm Infants

|  |  |  | For 100 g Of Powder | For 100 ml Of Liquid |
|---|---|---|---|---|
| Water |  |  | — | 85% |
| Maltodextrins |  |  | 28.91% | 4.33% |
| Fat mixture |  |  | 26.68% | 3.99% |
|  | a | b |  |  |
| Milkfat | 23.9% | 23.9% |  |  |
| MCT | 14.3% | 14.3% |  |  |
| Soy oil | 14.3% | 14.3% |  |  |
| Olive oil | 43% | 43% |  |  |
| Brain phospholipids | 4.5% | 3.2% |  |  |
| Fish oil | — | 1.3% |  |  |
| Skim milk (0.05% M.G.) |  |  | 14.58% | 2.19% |
| Lactalbumin |  |  | 12.13% | 1.82% |
| Lactose |  |  | 11.92% | 1.79% |
| Minerals |  |  | 3.26% | 0.49% |
| Calcium caseinate |  |  | 1.97% | 0.296% |
| Lecithin |  |  | 0.41% | 0.061% |
| Vitamins |  |  | 0.12% | 0.018% |
| Nucleotides and/or nucleosides |  |  | 0.0078% | 0.0012% |
| Ascorbile palmitate |  |  | 0.006% | 0.0009% |
| DL-Tocopherol |  |  | 0.001% | 0.0001% |

EXAMPLE 12

Example 12 is an adapted infant milk formula for the nutrition of normal infants which incorporates the fat mixtures of the present invention.

Adapted Infant Milk Formula

|  |  |  | For 100 g Of Powder | For 100 ml Of Liquid |
|---|---|---|---|---|
| Water |  |  | — | 87% |
| Lactose |  |  | 41.96% | 5.47% |
| Skim milk |  |  | 18.84% | 2.45% |
| Fat mixture |  |  | 27.76% | 3.67% |
|  | a | b |  |  |
| Brain phospholipids | 4.5% | 3.4% |  |  |
| MCT | 4.8% | 4.8% |  |  |
| Soy oil | 10.5% | 10.5% |  |  |
| Olive oil | 30.5% | 30.5% |  |  |
| Milkfat | 49.7% | 49.7% |  |  |
| Fish oil | — | 1.1% |  |  |
| Demineralized whey (65% of proteins) |  |  | 9.28% | 1.21% |
| Minerals salts |  |  | 1.11% | 0.14% |
| Lecithin |  |  | 0.31% | 0.04% |
| Vitamins |  |  | 0.069% | 0.009% |
| Nucleotides and/or nucleosides |  |  | 0.0078% | 0.001% |
| DL-Tocopherol |  |  | 0.003% | 0.0004% |
| Ascorbile palmitate |  |  | 0.001% | 0.0001% |

EXAMPLE 13

This is an infant adapted follow up milk formula which contains the fat mixtures of the present invention.

Infant Adapted Milk Formula

|  | For 100 g Of Powder | For 100 ml Of Liquid |
|---|---|---|
| Water | — | 85% |
| Skim milk | 31.69% | 4.75% |

Infant Adapted Milk Formula

| | | | For 100 g Of Powder | For 100 ml Of Liquid |
|---|---|---|---|---|
| Maltodextrins | | | 23.18% | 3.48% |
| Lactose | | | 19.28% | 2.89% |
| Fat mixture | | | 21.03% | 3.15% |
| | a | b | | |
| Brain phospholipids | 4.5% | 3.0% | | |
| Fat milk | 49.7% | 49.7% | | |
| MCT | 4.8% | 4.8% | | |
| Soy oil | 10.5% | 10.5% | | |
| Olive oil | 30.5% | 30.5% | | |
| Fish oil | — | 1.5% | | |
| Demineralized whey | | | 4.22% | 0.63% |
| Minerals salts | | | 0.41% | 0.061% |
| Lecithin | | | 0.14% | 0.021% |
| Vitamins | | | 0.069% | 0.01% |
| Nucleotides and/or nucleosides | | | 0.0078% | 0.0012% |
| DL-Tocopherol | | | 0.003% | 0.0004% |
| Ascorbile palmitate | | | 0.001% | 0.0001% |

EXAMPLE 14

This is a nutritional formula for infant nutrition which is lactose free and contains cow's protein and the fat mixture of the present invention.

Lactose Free Adapted Infant Formula Containing Cow's Protein

| | | | For 100 g Of Powder | For 100 ml Of Liquid |
|---|---|---|---|---|
| Water | | | — | 85% |
| Maltodextrins | | | 58.03% | 8.7% |
| Calcium caseinate (supplemented with L-cistine) | | | 16.7% | 2.51% |
| Fat mixture | | | 22.22% | 3.34% |
| | a | b | | |
| Brain phospholipids | 4.5% | 2.0% | | |
| MCT | 4.8% | 4.8% | | |
| Soy oil | 10.5% | 10.5% | | |
| Olive oil | 30.5% | 30.5% | | |
| Milkfat | 49.7% | 49.7% | | |
| Fish oil | — | 2.5% | | |
| Mineral salts | | | 2.18% | 0.33% |
| Lecithin | | | 0.69% | 0.103% |
| Vitamins | | | 0.069% | 0.01% |
| Carnitine | | | 0.0089% | 0.0013% |
| Nucleotides and/or nucleosides | | | 0.0078% | 0.0012% |
| DL-Tocopherol | | | 0.003% | 0.0004% |
| Ascorbile palmitate | | | 0.001% | 0.0001% |

EXAMPLE 15

A lactose free nutritional formula for infant nutrition which contains vegetal proteins and a fat mixture as disclosed in the present invention.

Lactose Free Adapted Infant Formula Containing Vegetable Protein

| | | | For 100 g Of Powder | For 100 ml Of Liquid |
|---|---|---|---|---|
| Water | | | — | 85% |
| Dextrinomaltose | | | 57.20% | 8.58% |
| Soy protein isolate | | | 16.67% | 2.5% |
| Fat mixture | | | 22.22% | 3.34% |
| | a | b | | |
| Brain phospholipids | 4.5% | 1.5% | | |
| MCT | 4.8% | 4.8% | | |
| Soy oil | 10.5% | 10.5% | | |
| Olive oil | 30.5% | 30.5% | | |
| Milkfat | 49.7% | 49.7% | | |
| Fish oil | — | 3.0% | | |
| Mineral salts | | | 3.04% | 0.46% |
| Lecithin | | | 0.69% | 0.103% |
| Vitamins | | | 0.069% | 0.01% |
| Carnitine | | | 0.0089% | 0.0013% |
| Nucleotides and/or nucleosides | | | 0.0078% | 0.0012% |
| DL-Tocopherol | | | 0.003% | 0.0004% |
| Ascorbile palmitate | | | 0.001% | 0.0001% |

EXAMPLE 16

A Hypoallergenic infant adapted milk formula which contains the fat mixtures of the present invention in order to provide adequate nutrition.

Hypoallergenic Adapted Infant Formula

| | | | For 100 g Of powder | For 100 ml of liquid |
|---|---|---|---|---|
| Water | | | — | 85% |
| Maltodextrins | | | 52.48% | 7.87% |
| Fat mixture | | | 21.27% | 3.19% |
| | a | b | | |
| Brain phospholipids | 4.5% | 1.0% | | |
| MCT | 23.9% | 23.9% | | |
| Fat milk | 19.1% | 19.1% | | |
| Olive oil | 39.1% | 39.1% | | |
| Soy oil | 13.4% | 13.4% | | |
| Fish oil | — | 3.5% | | |
| Lactalbumin enzymatic hydrolyzate | | | 12.31% | 1.85% |
| Casein enzymatic hydrolyzate | | | 5.16% | 0.77% |
| Corn starch | | | 4.87% | 0.73% |
| Minerals | | | 3.19% | 0.48% |
| Emulsifier | | | 0.60% | 0.09% |
| Vitamins | | | 0.069% | 0.01% |
| Lecithin | | | 0.0231% | 0.0035% |
| Carnitine | | | 0.0089% | 0.0013% |
| Nucleotides or nucleosides | | | 0.0078% | 0.0012% |
| DL-Tocopherol | | | 0.0038% | 0.0006% |
| Ascorbile palmitate | | | 0.0015% | 0.0002% |

EXAMPLE 17

A normoproteic diet composition for use in clinical nutrition of adults which contains a fat mixture as disclosed in the present invention in order to promote adequate nutrition.

EXAMPLE 18

A high protein diet for use in clinical nutrition of adults which contains a fat mixture of the type disclosed in the present invention.

| Hyperproteic Diet For Use In Clinical Nutrition | | | | |
|---|---|---|---|---|
| | | | For 100 g Of Powder | For 100 ml Of Liquid |
| Water | | | — | 77.28% |
| Maltodextrins | | | 50.6% | 11.49% |
| Lactalbumin | | | 15.96% | 3.64% |
| Calcium Caseinate | | | 13.08% | 3.14% |
| Fat mixture | | | 15.65% | 3.14% |
| | a | b | | |
| Olive oil | 33.4% | 33.4% | | |
| Soy oil | 11.5% | 11.5% | | |
| MCT | 9.5% | 9.5% | | |
| Fat milk | 41.1% | 41.1% | | |
| Brain phospholipids | 4.5% | 2.1% | | |
| Fish Oil | — | 2.4% | | |
| Minerals | | | 3.41% | 0.68% |
| Nucleotides or nucleosides | | | 0.75% | 0.15% |
| Soy lecithin | | | 0.5% | — |
| Emulsifier | | | — | 0.11% |
| Stabilizer | | | — | 0.02% |
| Vitamins | | | 0.026% | 0.005% |
| Ascorbile palmitate | | | 0.0232% | 0.0008% |
| DL-Tocopherol | | | 0.0008% | 0.0002% |

EXAMPLE 19

A peptide and MCT containing diet composition for use in the clinical nutrition of adults which contains a fat mixture of the type disclosed in the present invention.

| Normoproteic Diet For Use In Clinical Nutrition | | | | |
|---|---|---|---|---|
| | | | For 100 g Of Powder | For 100 ml Of Liquid |
| Water | | | — | 78.7% |
| Maltodextrins | | | 2.13% | 11.2% |
| Lactalbumin | | | 11.63% | 2.48% |
| Fat mixture | | | 20.94% | 3.5% |
| | a | b | | |
| Olive oil | 33.4% | 33.4% | | |
| Soy oil | 11.5% | 11.5% | | |
| MCT | 9.5% | 9.5% | | |
| Fat milk | 41.4% | 41.4% | | |
| Brain phospholipids | 4.5% | 2.4% | | |
| Fish Oil | — | 2.1% | | |
| Calcium caseinate | | | 10.05% | 2.14% |
| Minerals | | | 3.79% | 0.79% |
| Nucleotides or nucleosides | | | 0.75% | 0.15% |
| Soy lecithin | | | 0.66% | — |
| Emulsifier | | | — | 0.136% |
| Stabilizer | | | — | 0.02% |
| Vitamins | | | 0.026% | 0.005% |
| Ascorbile palmitate | | | 0.0232% | 0.0008% |
| DL-Tocopherol | | | 0.0008% | 0.0002% |

| Peptidic-MCT Diet For Use In Clinical Nutrition | | | | |
|---|---|---|---|---|
| | | | For 100 g Of Powder | For 100 ml Of Liquid |
| Water | | | — | 77.83% |
| Maltodextrins | | | 51.62% | 11.43% |
| Casein hydrolyzate | | | 25.80% | 5.72% |
| Fat mixture | | | 12.44% | 2.76% |
| | a | b | | |
| Olive oil | 36.3% | 36.3% | | |
| Soy oil | 12.4% | 12.4% | | |
| Fat milk | 18.1% | 18.1% | | |
| MCT | 28.7% | 28.7% | | |
| Brain phospholipids | 4.5% | 1.9% | | |
| Fish Oil | — | 2.6% | | |
| Minerals | | | 5.02% | 1.11% |
| Nucleotides or nucleosides | | | 0.75% | 0.17% |
| Soy lecithin | | | 0.50% | — |
| Emulsifier | | | — | 0.11% |
| L-cistine | | | 0.20% | 0.04% |
| Stabilizer | | | — | 0.02% |
| Vitamins | | | 0.026% | 0.0058% |
| Ascorbile palmitate | | | 0.0232% | 0.0051% |
| DL-Tocopherol | | | 0.0008% | 0.0002% |

EXAMPLE 20

A complete diet composition for use in the clinical nutrition of adult patients with liver disease which contains the fat mixture of the present invention.

| Complete Diet For Use In Clinical Nutrition Of Patients With Liver Disease | | | | |
|---|---|---|---|---|
| | | | For 100 g Of Powder | For 100 ml Of Liquid |
| Water | | | — | 76.36% |
| Maltodextrins | | | 72.13% | 17.04% |
| Fat mixture | | | 7.48% | 1.77% |
| | a | b | | |
| MCT | 59.2% | 59.2% | | |
| Corn oil | 36.3% | 36.3% | | |
| Brain phospholipids | 4.5% | 2.6% | | |
| Fish Oil | — | 1.9% | | |
| Lactalbumin | | | 7.26% | 1.72% |
| Calcium caseinate | | | 6.27% | 1.48% |
| Minerals | | | 2.94% | 0.69% |
| L-leucine | | | 1.16% | 0.27% |
| L-Valine | | | 0.87% | 0.21% |
| L-isoleucine | | | 0.87% | 0.21% |
| Nucleotides or nucleosides | | | 0.75% | 0.18% |
| Soy lecithin | | | 0.22% | — |
| Emulsifier | | | — | 0.05% |
| Stabilizer | | | — | 0.01% |
| Vitamins | | | 0.026% | 0.006% |
| Ascorbile palmitate | | | 0.0197% | 0.005% |
| DL-Tocopherol | | | 0.0003% | 0.00007% |

EXAMPLE 21

A group of weanling rats, which were 21 days old, were given a diet which contained a fat mixture as described in the present invention. The diet consisted of a standard rat diet supplemented with 10% fat. Of the fat present in the diet, 4.5% was made up of polyunsaturated fats obtained from calf brain. The fatty acid composition of this fat mixture was identical to that disclosed in Example 13.

Another group of weanling rats was fed for the same period with the same diet, with the exception that this diet was not supplemented with the source of polyunsaturated fatty acids. This latter group was considered the control.

The analyses of the plasma fatty acids indicates that the level of docosahexaenoic acid (22:6n3) is significantly increased in the animals which are fed the diet which has been enriched with polyunsaturated fatty acids as compared to the animals which received the control diet. No change was observed in the plasma levels of eicosatrienoic acid (20:3n6) and arachidonic acid (20:4n6) for animals fed the diet of the present invention. This is in contrast to the use of other sources of polyunsaturated fatty acids (i.e. Fish oil) where the levels of these compounds are reduced. The following table presents the plasma fatty acid levels for the animals in the experiment.

|        | Control % | PUFA Diet %   |
|--------|-----------|---------------|
| 16:0   | 17.7      | 17.9          |
| 16:1   | 1.1       | 0.9           |
| 18:0   | 17.0      | 16.1          |
| 18:1   | 15.8      | 16.6          |
| 18:2   | 11.8      | 11.3          |
| 20:3n6 | 1.3       | 1.1           |
| 20:4n6 | 31.5      | 30.0          |
| 22:4n6 | 0.4       | 0.5           |
| 22:6n3 | 2.5 + 0.1 | 3.0 ± 0.1*    |

*$p < 0.05$ with respect to control

What is claimed:

1. A fat mixture for use in a nutritional product, comprising:
   a) between about 30.5% and about 43.0% by weight olive oil per 100 g of mixture,
   b) between about 10.5% and about 14.3% by weight soy oil,
   c) between about 18.1% and about 49.7% by weight milk fat,
   d) between about 4.8% and about 28.7% by weight medium chain triglycerides,
   e) between about 1.0% and 4.5% by weight phospholipids and
   f) up to about 3.5% by weight fish oil.

2. The fat mixture of claim 1, wherein:
   a) said olive oil comprises about 43.0% per 100 g of mixture,
   b) said soy oil comprises about 14.3%,
   c) said milk fat comprises about 23.9%,
   d) said medium chain triglycerides comprise about 14.3%,
   e) said phospholipids comprise between about 3.2% and 4.5% and
   f) said fish oil comprises up to about 1.3%.

3. The fat mixture of claim 1, wherein:
   a) said olive oil comprises about 30.5% per 100 g of mixture,
   b) said soy oil comprises about 10.5%,
   c) said milk fat comprises about 49.7%,
   d) said medium chain triglycerides comprise about 4.8%,
   e) said phospholipids comprise between about 3.4% and 4.5% and
   f) said fish oil comprises up to about 1.1%.

4. The fat mixture of claim 1, wherein:
   a) said olive oil comprises about 30.5% per 100 g of mixture,
   b) said soy oil about 10.5%,
   c) said milk fat about 49.7%,
   d) said medium chain triglycerides comprise about 4.8%,
   e) said phospholipids comprise between about 3.0% and 4.5% and
   f) said fish oil comprises up to about 1.5%.

5. The fat mixture of claim 1, wherein:
   a) said olive oil comprises about 30.5% per 100 g of mixture,
   b) said soy oil comprises about 10.5%,
   c) said milk fat comprises about 49.7%,
   d) said medium chain triglycerides comprise about 4.8%,
   e) said phospholipids comprise between about 2.0% and 4.5% and
   f) said fish oil comprises up to about 2.5%.

6. The fat mixture of claim 1, wherein:
   a) said olive oil comprises about 30.5% per 100 g of mixture,
   b) said soy oil comprises about 10.5%,
   c) said milk fat comprises about 49.7%,
   d) said medium chain triglycerides comprise about 4.8%,
   e) said phospholipids comprise between about 1.5% and 4.5% and
   f) said fish oil comprises up to about 3.0%.

7. The fat mixture of claim 1, wherein:
   a) said olive oil comprises about 39.1% per 100 g of mixture,
   b) said soy oil comprises about 13.4%,
   c) said milk fat comprises about 19.1%,
   d) said medium chain triglycerides comprise about 23.9%,
   e) said phospholipids comprise between about 1.0% and 4.5% and
   f) said fish oil comprises up to about 3.5%.

8. The fat mixture of claim 1, wherein:
   a) said olive oil comprises about 33.4% per 100 g of mixture,
   b) said soy oil comprises about 11.5%,
   c) said milk fat comprises about 41.1%,
   d) said medium chain triglycerides comprise about 9.5%,
   e) said phospholipids comprise between about 2.4% and 4.5% and
   f) said fish oil comprises up to about 2.1%.

9. The fat mixture of claim 1, wherein:
   a) said olive oil comprises about 33.4% per 100 g of mixture,
   b) said soy oil comprises about 11.5%,
   c) said milk fat comprises about 41.1%,
   d) said medium chain triglycerides comprise about 9.5%,
   e) said phospholipids comprise between about 2.1% and 4.5% and
   f) said fish oil comprises up to about 2.4%.

10. The fat mixture of claim 1, wherein:
    a) said olive oil comprises about 36.3% per 100 g of mixture,
    b) said soy oil comprises about 12.4%,
    c) said milk fat comprises about 18.1%,
    d) said medium chain triglycerides comprise about 28.7%,
    e) said phospholipids comprise between about 1.9% and 4.5% and
    f) said fish oil comprises up to about 2.6%.

11. A fat mixture for use in a nutritional product, comprising:

a) about 36.3% by weight corn oil per 100 g of mixture,
b) about 59.2% medium chain triglycerides,
c) between about 2.6% and 4.5% phospholipids and
f) up to about 1.9% fish oil.

12. An artificial nutritional formula, comprising:
a) about 28.91% by weight maltodextrins per 100 g of powder formula,
b) about 26.68% of the fat mixture of claim 2,
c) about 14.58% skim milk,
d) about 12.13% lactalbumin,
e) about 11.92% lactose,
f) about 3.26% minerals,
g) about 1.97% calcium caseinate,
h) about 0.41% lecithin,
i) about 0.12% vitamins,
j) up to about 0.0078% nucleotides,
k) up to about 0.0078% nucleosides,
l) about 0.006% ascorbile palmitate and
m) about 0.001% DL-tocopherol.

13. An artificial nutritional formula, comprising:
a) about 41.96% by weight lactose per 100 g of powder formula,
b) about 18.84% skim milk,
c) about 27.76% of the fat mixture of claim 3,
d) about 9.28% demineralized whey,
e) about 1.11% minerals,
f) about 0.31% lecithin,
g) about 0.069% vitamins,
h) up to about 0.0078% nucleotides,
i) up to about 0.0078% nucleosides,
j) about 0.003% DL-tocopherol and
k) about 0.001% ascorbile palmitate.

14. An artificial nutritional formula, comprising:
a) about 31.69% by weight skim milk per 100 g of powder formula,
b) about 23.18% maltodextrins,
c) about 19.28% lactose,
d) about 21.03% of the fat mixture of claim 4,
e) about 4.22% demineralized whey,
f) about 0.41% minerals,
g) about 0.14% lecithin,
h) about 0.069% vitamins,
i) up to about 0.0078% nucleotides,
j) up to about 0.0078% nucleosides,
k) about 0.003% DL-tocopherol and
l) about 0.001% ascorbile palmitate.

15. An artificial nutritional formula, comprising:
a) about 58.03% by weight maltodextrins per 100 g of powder formula,
b) about 16.7% calcium caseinate,
c) about 22.22% of the fat mixture of claim 5,
d) about 2.18% minerals,
e) about 0.69% lecithin,
f) about 0.069% vitamins,
g) about 0.0089% carnitine,
h) up to about 0.0078% nucleotides,
i) up to about 0.0078% nucleosides,
j) about 0.003% DL-tocopherol and
k) about 0.001% ascorbile palmitate.

16. An artificial nutritional formula, comprising:
a) about 57.20% by weight dextrinomaltose per 100 g of powder formula,
b) about 16.67% soy protein isolate,
c) about 22.22% of the fat mixture of claim 6,
d) about 3.04% minerals,
e) about 0.69% lecithin,
f) about 0.069% vitamins,
g) about 0.0089% carnitine,
h) up to about 0.0078% nucleotides,
i) up to about 0.0078% nucleosides,
j) about 0.003% DL-tocopherol and
k) about 0.001% ascorbile palmitate.

17. An artificial nutritional formula, comprising:
a) about 52.48% by weight maltodextrins per 100 g of powder formula,
b) about 21.27% of the fat mixture of claim 7,
c) about 12.31% lactalbumin enzymatic hydrolysate,
d) about 5.16% casein enzymatic hydrolysate,
e) about 4.87% corn starch,
f) about 3.19% minerals,
g) about 0.6% emulsifier,
h) about 0.069% vitamins,
i) about 0.0231% lecithin,
j) about 0.0089% carnitine,
k) up to about 0.0078% nucleotides,
l) up to about 0.0078% nucleosides,
m) about 0.0038% DL-tocopherol and
n) about 0.0015% ascorbile palmitate.

18. An artificial nutritional formula, comprising:
a) about 52.13% by weight maltodextrins per 100 g of powder formula,
b) about 11.63% lactalbumin,
c) about 20.94% of the fat mixture of claim 8,
d) about 10.05% calcium caseinate,
e) about 3.79% minerals,
f) about 0.75% nucleotides or nucleosides,
g) about 0.66% soy lecithin,
h) about 0.026% vitamins,
i) about 0.0232% ascorbile palmitate and
j) about 0.0008% DL-tocopherol.

19. An artificial nutritional formula, comprising:
a) about 50.6% by weight maltodextrins per 100 g of powder formula,
b) about 15.96% lactalbumin,
c) about 13.08% calcium caseinate,
d) about 15.65% of the fat mixture of claim 9,
e) about 3.41% minerals,
f) about 0.75% nucleotides or nucleosides,
g) about 0.5% soy lecithin,
h) about 0.026% vitamins,
i) about 0.0232% ascorbile palmitate and
j) about 0.0008% DL-tocopherol.

20. An artificial nutritional formula, comprising:
a) about 51.62% by weight maltodextrins per 100 g of powder formula,
b) about 25.80% casein hydrolysate, c) about 12.44% of the fat mixture of claim 10,
d) about 5.02% minerals,
e) about 0.75% nucleotides or nucleosides,
f) about 0.5% soy lecithin,
g) about 0.20% L-cysteine,
h) about 0.026% vitamins,
i) about 0.0232% ascorbile palmitate and
j) about 0.0008% DL-tocopherol.

21. An artificial nutritional formula, comprising:
a) about 72.13% by weight maltodextrins per 100 g of powder formula,
b) about 7.48% of the fat mixture of claim 11,
c) about 7.26% lactalbumin,
d) about 6.27% calcium caseinate,
e) about 2.94% minerals,
f) about 1.16% L-leucine,
g) about 0.87% L-valine,
h) about 0.87% L-isoleucine,
i) about 0.75% nucleotides or nucleosides,
j) about 0.22% soy lecithin,
k) about 0.026% vitamins,
l) about 0.0197% ascorbile palmitate and
m) about 0.0003% DL-tocopherol.

* * * * *